(12) United States Patent
Lafontaine

(10) Patent No.: US 6,416,523 B1
(45) Date of Patent: Jul. 9, 2002

(54) METHOD AND APPARATUS FOR CREATING CHANNELS THROUGH VASCULAR TOTAL OCCLUSIONS

(75) Inventor: Daniel M. Lafontaine, Plymouth, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/678,147

(22) Filed: Oct. 3, 2000

(51) Int. Cl.$^7$ ................................................ A61B 17/22
(52) U.S. Cl. ...................... 606/159; 600/373; 600/547; 607/28
(58) Field of Search ................................. 606/159, 170, 606/171; 604/22; 607/9, 11, 28; 600/373, 547

(56) References Cited

U.S. PATENT DOCUMENTS

| | | | |
|---|---|---|---|
| 4,784,636 A | * 11/1988 | Rydell | 606/159 |
| 4,895,560 A | * 1/1990 | Papantonakos | 606/159 |
| 5,364,393 A | 11/1994 | Auth et al. | |
| 5,665,098 A | * 9/1997 | Kelly et al. | 606/159 |
| 5,941,869 A | * 8/1999 | Patterson et al. | 604/22 |
| 6,238,389 B1 | * 5/2001 | Paddock et al. | 600/146 |

* cited by examiner

*Primary Examiner*—Kennedy Schaetzle
*Assistant Examiner*—Kristen Droesch
(74) *Attorney, Agent, or Firm*—Christensen O'Connor Johnson Kindness PLLC

(57) ABSTRACT

A method and apparatus for creating a lumen through a total vascular occlusion. A directional cutter is advanced ahead of a number of proximal electrodes that engage a vessel wall. Blood in the vessel between the directional cutter and the proximal electrodes is removed by sealing the vessel with an occluding balloon and pumping a bio-compatible gas into the vessel to displace the blood. A signal source is applied to the directional cutter and used to measure the impedance between the directional cutter and each of the proximal electrodes. If the cutter engages a vessel wall, the impedance between the cutter and the proximal electrode decreases. A physician monitors the impedance to know when the vessel wall is engaged and turns the direction of the cutter away from the vessel wall such that the cutter continues creating a lumen within the occluding material. Once a lumen has been created in the occluding material, the cutter and electrodes are removed from the vessel and the vessel is treated with a conventional atherectomy device. In another embodiment of the invention, the signal source supplies a pacing signal to the directional cutter. If the cutter is embedded within an occlusion, the heart is not captured by the pacing signal. Once the cutter contact the vessel wall, the heart is captured and the physician changes the direction of the cutter to continue creating the lumen within the occlusion.

11 Claims, 4 Drawing Sheets

METHOD AND APPARATUS FOR CREATING CHANNELS THROUGH VASCULAR TOTAL OCCLUSIONS

FIELD OF THE INVENTION

The present invention relates to medical devices, and in particular to devices for creating lumens in totally occluded vessels.

BACKGROUND OF THE INVENTION

Balloon angioplasty and rotational ablation are two commonly performed, minimally invasive surgical techniques used to create lumens in a patient's occluded blood vessel. With these techniques, a guide catheter is usually inserted into the patient's femoral artery and routed through the vasculature to the point of an occlusion. Next, a guide wire is inserted through the guide catheter and advanced to a point past the occlusion. A treatment device, either an angioplasty balloon or a rotational ablation device, is then run over the guide wire to compress or remove the occluding material from the vessel. While these minimally invasive procedures often eliminate the need to perform more invasive surgery, the procedures are not often used when a patient's vessel is totally occluded because the guide wire cannot be advanced past the occlusion. Therefore, the majority of total occlusions still are treated using more invasive surgical techniques.

Given the benefits associated with less invasive atherectomy procedures, there is a need to adapt these minimally invasive, percutaneous procedures to the situation where a vessel is totally occluded.

SUMMARY OF THE INVENTION

The present invention is a technique for guiding a cutting device through a total vascular occlusion without perforating a vessel wall. An eccentric cutter is supplied with a high frequency electronic signal for use in determining the impedance between the cutter and a number of wire electrodes disposed proximally of the cutter.

In the embodiment, the proximal electrodes are formed as an expandable wire stent wherein the tips of the wires engage but do not perforate the surrounding vessel wall. The impedance between the eccentric cutter and each of the electrodes is determined as the cutter is advanced through the occlusion. Cutting proceeds until the cutter engages the vessel wall and the impedance between the eccentric cutter and the proximal electrodes decreases. At this time, the direction of the eccentric cutter is changed and cutting continues along the length of the total occlusion.

In accordance with another aspect of the present invention, carbon dioxide is delivered to the cutting area to remove blood between the cutter and the proximal electrodes.

In yet another embodiment of the invention, a low level pacing signal is supplied to the cutter end and it is determined if the pacing signal captures the heart. If no capture occurs, the cutter is advanced. Once capture occurs, the direction of the cutter is changed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
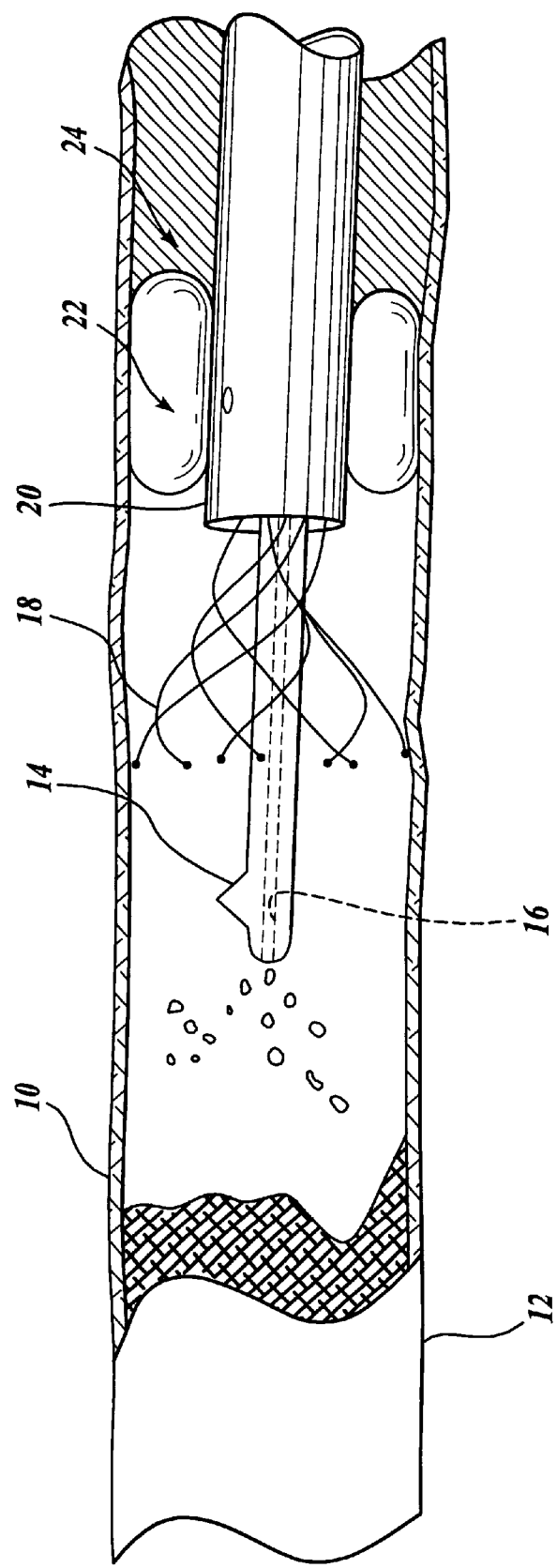
FIG. 1 illustrates a first embodiment of the invention for crossing a total vascular occlusion.

The present invention is a method and apparatus for percutaneously crossing a total occlusion in a patient's blood vessel. As shown in FIG. 1, a blood vessel 10 is blocked by an occlusion 12 that prevents blood from flowing within the vessel. Because the occlusion 12 totally blocks the vessel, it is not possible to pass a guide wire through the occlusion in order to treat the occlusion with conventional intravascular atherectomy methods such as balloon angioplasty or using a rotational ablation device.

In order to create a lumen within the occlusion, the present invention utilizes an eccentric or directional cutter 14 that is routed within a guide catheter 20 to the point of the occlusion. The eccentric cutter creates a lumen through the total occlusion 12 and generally moves toward a vessel wall as the cutter is advanced by a physician. To prevent the cutter from perforating the vessel wall, the position of the cutter with respect to the vessel wall is monitored by measuring the impedance between the cutter and a number of electrodes that contact the vessel wall. It has been determined that the impedance of plaque or other occluding substances in the vessel is relatively high compared with the impedance of the vessel wall or blood. By displacing the blood between the cutter and the electrodes, the impedance can be monitored to detect when the cutter is within the occluding material and when it engages the vessel wall.

To displace the blood within the area between the cutter and the number of proximal electrodes 18, the catheter 20 has an occlusion balloon 22 that prevents the blood 24 in the vessel from flowing into the area of the occlusion. To remove the blood between the occlusion 12 and the balloon 22, the cutter 14 includes a lumen 16 through which a low pressure, bio-compatible gas such as carbon dioxide is delivered. The gas displaces the blood from the vessel 10 in the area of the occlusion 12. Any excess gas delivered to the site of the occlusion is removed by a vent at the proximal end of vessel via the guide catheter 20 or is dissolved in the blood.

The proximal electrodes 18 are preferably configured as an expandable wire stent. Each of the wires that comprise the stent are insulated over their length so as not to make electrical contact between the wires. The tips of the wires are exposed and may be relatively sharp such that as the stent expands, the wires make a good electrical connection to the wall but not to perforate it.

To detect where the cutter 14 is with respect to the proximal electrodes 18, a high-frequency electronic signal is applied to the cutter 14 in order to measure the impedance between the cutter and the proximal electrodes 18. The frequency of the signal is preferably above 50 kHz so as not to induce fibrillation, and is more preferably about 1 MHz.

Figure 2:
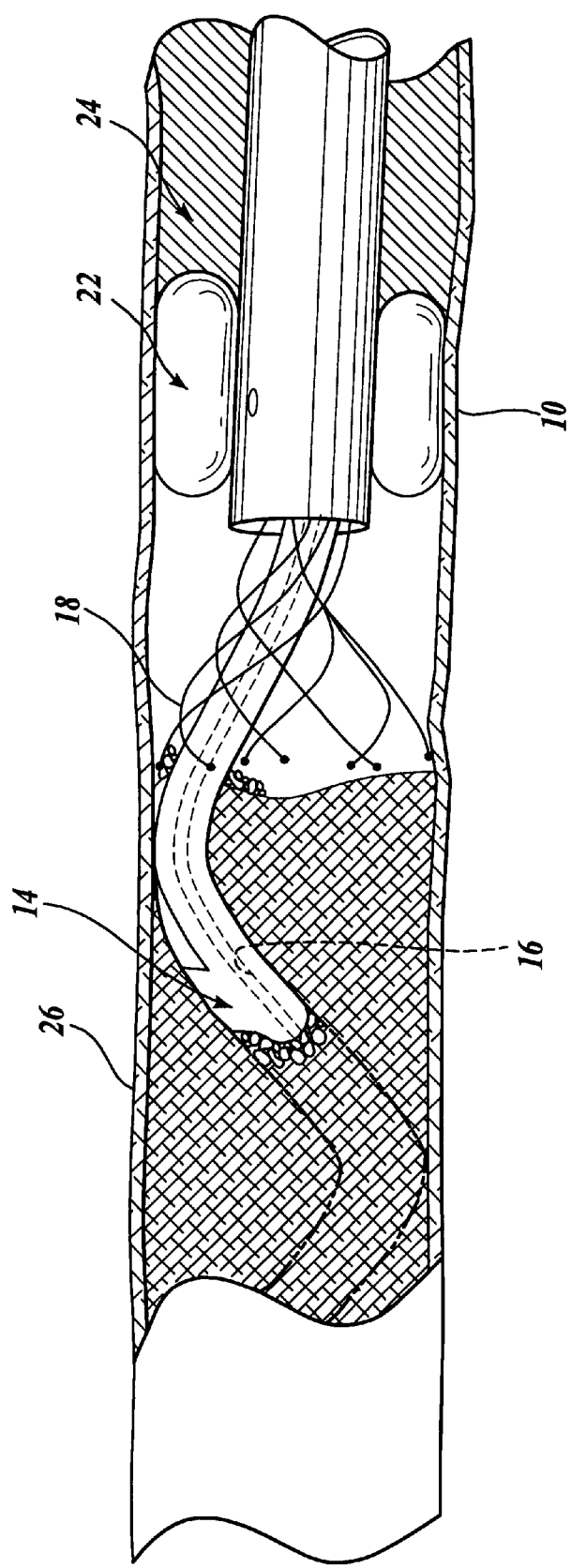
FIG. 2 is a path taken by a directional cutter through an occlusion in accordance with the present invention.

FIG. 2 shows in greater detail how the directional cutter 14 is advanced through the total occlusion material 12 with the vessel 10. As indicated above, carbon dioxide is forced through a lumen 16 within the directional cutter 14 to displace blood from the area between the distal end of cutter 14 and the proximal electrodes 18. The directional cutter 14 creates a lumen in the occluding material until the directional cutter nears or engages the vessel wall at a point 26. Here, the impedance between the directional cutter 14 and the proximal electrodes 18 is substantially reduced compared with the impedance when the cutter 14 is embedded within the occluding material 12. Therefore, the physician rotates the directional cutter 14 by 180° and cutting continues towards the opposite vessel wall until the impedance between the directional cutter 14 and the proximal electrodes 18 again indicates the cutter has contacted the vessel wall. The physician then reverses the directional cutter and the process repeats itself. As will be appreciated, a zigzag path is created through the occluding material 12 by ablating a lumen until the directional cutter nears or engages the vessel wall and then reversing the direction of the directional cutter.

Once the directional cutter 14 has passed all the way through the occluding material 12, the directional cutter 14 and proximal electrodes 18 can be withdrawn from the guide catheter 20. A guide wire can then be advanced through the lumen created in the occlusion and any occluding material that remains can be treated with conventional atherectomy devices such as an angioplasty balloon or a rotational ablation device.

Figure 3:
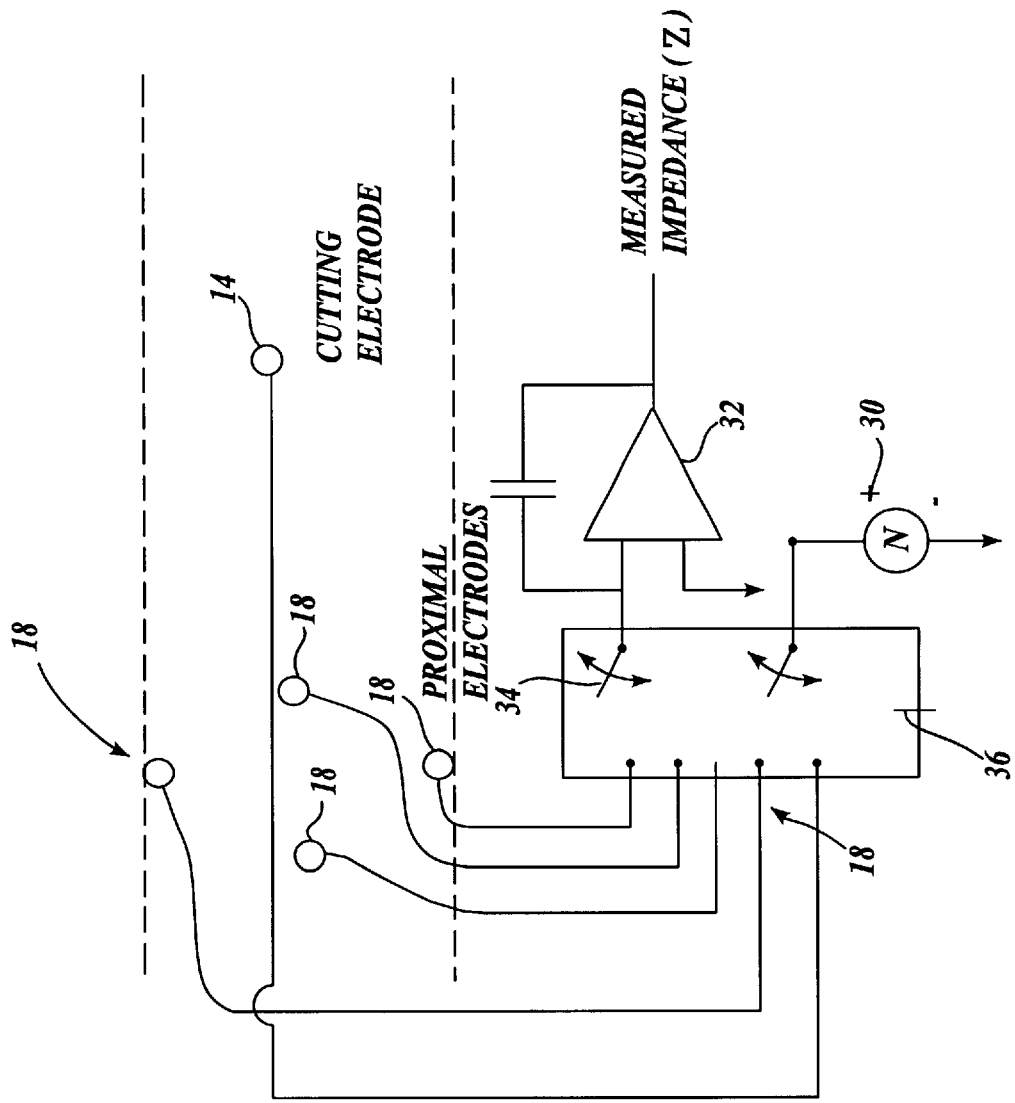
FIG. 3 is an electrical diagram of a system for determining the impedance between a directional cutter and one or more proximal electrodes in accordance with one embodiment of the present invention.

FIG. 3 illustrates the method of detecting when the directional cutter 14 is nearing a vessel wall. As indicated above, the impedance of occluding material such as plaque in a vessel is many times higher than the impedance of a vessel wall or that of blood. To provide an indication of the orientation/position of a directional cutter, a signal source 30 is coupled by a switch/multiplexer 36 to the directional cutter 14 or any of the proximal electrodes 18. An amplifier 32 has an input 34 that can be coupled by the switch/multiplexer 36 to any of the proximal electrodes 18 or to the directional cutter 14. The signal produced by the amplifier 32 is proportional to the amount of current flowing into the input 34 and is therefore indicative of the impedance between the signal source 30 and the electrode to which the input 34 is connected.

In order to measure the impedance between the directional cutter 14 and any of the proximal electrodes 18, the signal source 30 is applied to the directional cutter 14 and the input 34 of the amplifier 32 is connected to each of the proximal electrodes 18 in turn. When the directional cutter 14 is embedded in the occluding material, the impedance between the directional cutter and any of the proximal electrodes will be relatively high. However, as the directional cutter moves within the vessel, the distance between the directional cutter and each of the proximal electrodes will change. Therefore, the impedance, which is proportional to the distance between the directional cutter and each of the proximal electrodes will also vary. Therefore, by monitoring impedance, the physician is able to determine the orientation of the directional cutter. Once the cutter engages the vessel wall, the impedance drops significantly and the physician then knows to turn the directional cutter away from the vessel wall and to continue to advance it through the vessel.

In addition, it may be desirable to determine the relative impedance between the different proximal electrodes. In that case, the signal source 30 is connected by the switch/multiplexer 36 to one of the proximal electrodes and the input 34 of the amplifier 32 is connected by the switch/multiplexer 36 to another of the proximal electrodes in order to determine the impedance between them. If each of the proximal electrodes is embedded in healthy arterial tissue, the impedance between each of the proximal electrodes should be minimal. However, if one of the proximal electrodes has not engaged the vessel wall or is embedded in plaque, then the impedance between that electrode and its neighbors may vary. If it is determined from the impedance measurement that a proximal electrode is not embedded in the vessel wall, that electrode may be disregarded for the purposes of informing the physician of the orientation of the cutter and which way to steer it.

Figure 4B:
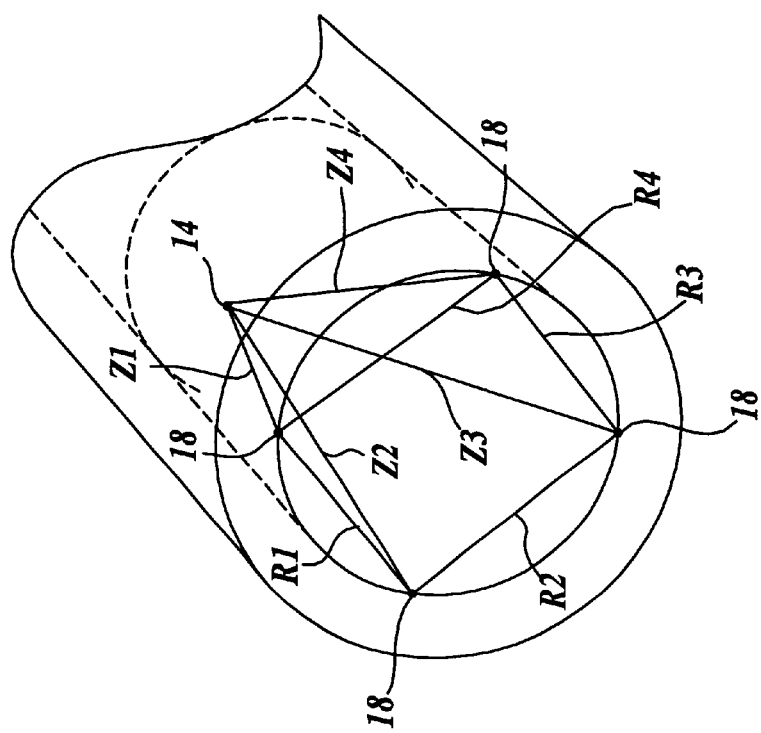
FIG. 4 illustrates a representative display that shows the relative impedance between the directional cutter and the one or more proximal electrodes in order to guide a physician advancing the cutter.
Figure 4A:
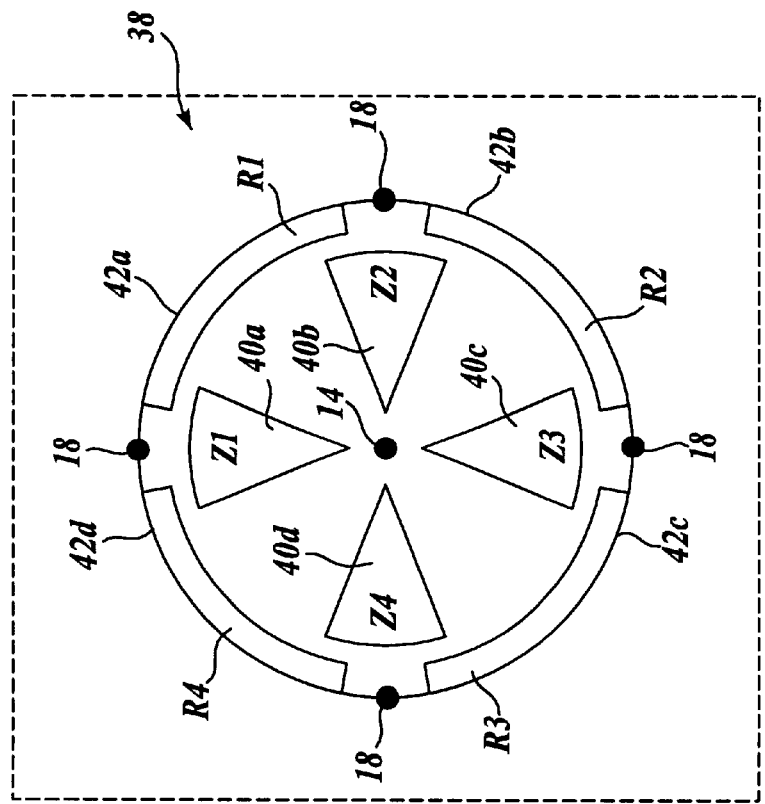

FIG. 4 illustrates a representative display that can be created with the impedance measurement. A display 38 to be shown on a computer monitor or other display graphically illustrates the impedance between the center directional cutter 14 and each of the proximal electrodes 18, labeled $Z_1$–$Z_4$. The impedance between the directional cutter 14 as depicted at the center of the display and each depicted individual proximal electrode 18 around the perimeter of the display can be shown as a pie-shaped element 40a–40d. The color or gray scale of the elements 40a–40d are dependent on the measured impedance, $Z_1$–$Z_4$. If the impedance remains relatively high, the physician can continue to ablate in the current direction. However, once the impedance between the directional cutter and any of the individual electrodes becomes substantially smaller, the physician can detect that the cutter is nearing a vessel wall. Once the cutter makes electrical contact with the vessel wall, the impedance between the cutter and the closest proximal electrode should decrease to a minimum. The physician then rotates the directional cutting mechanism and continues cutting through the occluding material. Once the directional cutter has passed all the way through the occluding material, the occlusion can be treated in a conventional manner using guide wires and balloons or atherectomy devices. In addition, the display 38 can include a number of sectors 42a–42d that represent the impedance between each of the proximal electrodes labeled $R_1$–$R_4$. As indicated above, if each of the electrodes is embedded in the vessel wall, the impedance should be minimal. However, if an electrode is not making contact with the vessel wall, the sectors 42a–42d will appear in a different color or gray scale. The physician will then know by looking at the display to be wary when judging the position of the cutter based on impedance measurements made with the proximal electrode in question.

As can be seen from the above, the present invention provides a simple method of allowing a physician to create a lumen through a total vascular occlusion. By monitoring the impedance between a directional cutter and a number of proximal electrodes, the physician can determine when the cutter makes contact with the vessel wall and can turn the cutter appropriately to continue ablating a lumen through the occluding material.

While the preferred embodiment of the invention has been illustrated and described, it will be appreciated that various changes can be made therein without departing from the scope of the invention. For example, although the embodiment described illustrates the use of four proximal electrodes, a greater number such as eight or twelve equally spaced around the vessel wall may be desirable. Furthermore, the directional cutter used is not limited to those that cut only to one side or another. Any cutter whose direction of cutting can be controlled may be used. Finally, the invention may also be practiced by coupling a pacing signal to the direction cutter. A pacing signal that causes the heart to beat at an increased rate, such as 200 beats per minute can be applied to the cutter. If the cutter is embedded in occluding material, the heart will not be captured. Once the cutter nears the vessel wall, the pacing signal can reach the heart via the conductive blood vessels and the heart rate increases. Therefore, the physician only need monitor the heart rate to determine if the cutter has reached the vessel wall., Once the vessel wall is reached, the physician changes the cutting direction of the burr.

The embodiments of the invention in which an exclusive property or privilege is claimed are defined as follows:

1. A system for creating a lumen through a total vascular occlusion, comprising:
   a directional cutter that directionally creates a lumen within an occlusion;
   a plurality of isolated electrodes that are adapted to contact a vessel wall proximal to the cutter;
   a signal source for supplying current between the cutter and the plurality of electrodes; and
   a circuit for measuring an impedance between the cutter and the plurality of electrodes, wherein the impedance varies when the cutter is in the occlusion versus when the cutter is in contact with the vessel wall such that the direction of the cutter can be changed to advance the cutter through the total vascular occlusion.

2. The system of claim 1, further comprising:
   a catheter through which the cutter and plurality of electrodes are routed, the catheter including a sealing mechanism for selectively occluding the vessel proximal to the cutter.

3. The system of claim 1, further comprising:
   a lumen for delivering a bio-compatible gas to the vessel to displace blood between the cutter and the plurality of electrodes.

4. The system of claim 1, further comprising:
   one or more switches that selectively couple the signal source and impedance measuring circuit between the cutter and each of the plurality of electrodes sequentially, in order to detect the impedance between the cutter and each of the plurality of electrodes.

5. The system of claim 1, further comprising a display that visually indicates the relative impedance between the cutter and each of the plurality of electrodes.

6. The system of claim 1, wherein the plurality of electrodes are formed as an expanding stent.

7. A system for creating a lumen through a total vascular occlusion, comprising:
   a directional cutter that creates a lumen within the occlusion;
   a plurality of isolated electrodes that are adapted to contact a vessel wall;
   a signal source for supplying an electrical signal between the cutter and the plurality of electrodes; and
   a circuit for measuring an impedance between the cutter and the plurality of electrodes in order to determine when the cutter engages the vessel wall so that the direction of the cutter can be changed to advance through the occlusion.

8. A system for creating a lumen through a total occlusion, comprising:
   a directional cutter that creates a lumen within the total occlusion;
   a plurality of isolated electrodes at least some of which are adapted to contact a vessel wall proximal to the cutter;
   a signal source that supplies an electrical signal between the directional cutter and the plurality of isolated electrodes;
   a circuit for indicating a relative impedance between the cutter and the plurality of isolated electrodes, wherein said impedance drops between the cutter and an isolated electrode that is nearest said cutter when said cutter engages a vessel wall, said directional cutter being turned away from said nearest isolated electrode after the cutter engages a vessel wall to continue cutting through said total occlusion.

9. A system for creating a lumen through a total vascular occlusion, comprising:
   a cutter that creates a lumen within an occlusion;
   a plurality of isolated electrodes formed as an expanding stent that are adapted to contact a vessel wall proximal to the cutter;
   a signal source for supplying current between the cutter and the plurality of electrodes; and
   a circuit for measuring an impedance between the cutter and the plurality of electrodes, wherein the impedance varies when the cutter is in the occlusion versus when the cutter is in contact with the vessel wall.

10. A method of creating a lumen within a total vascular occlusion, comprising:
    advancing a cutter into the occlusion;
    placing a plurality of electrodes proximal to the cutter;
    displacing blood in the vessel between the cutter and the plurality of electrodes;
    measuring the impedance between the cutter and the plurality of electrodes; and
    changing the direction of the cutter within the occlusion when the impedance indicates the cutter has engaged the vessel wall.

11. A system for creating a lumen through a total vascular occlusion, comprising:
    a cutter that creates a lumen within an occlusion;
    a signal source coupled to the cutter for applying a pacing signal to the cutter, wherein said lumen pacing signal causes a change in a heart rate of a patient when the cutter engages a vessel wall and does not change the heart rate when the cutter is embedded in the occlusion; and
    a heart rate detector that monitors a change in heart rate such that a physician can change the direction of the cutter in a vessel upon detection of the cutter engaging the vessel wall.

* * * * *